United States Patent [19]

Stewart

[11] Patent Number: 5,916,541
[45] Date of Patent: *Jun. 29, 1999

[54] WATER RESISTANT SUNSCREEN AND INSECT REPELLENT COMPOSITION

[76] Inventor: Ernest G. Stewart, 101 West Club Dr., Thomasville, Ga. 31792

[ * ] Notice: This patent is subject to a terminal disclaimer.

[21] Appl. No.: 08/640,478

[22] Filed: May 1, 1996

Related U.S. Application Data

[63] Continuation-in-part of application No. 08/154,584, Nov. 18, 1993, Pat. No. 5,518,712, which is a continuation-in-part of application No. 07/904,514, Jun. 25, 1992, abandoned.

[51] Int. Cl.$^6$ .................................................. A61K 7/42
[52] U.S. Cl. ............................................. 424/59; 514/844
[58] Field of Search ................................. 424/59; 514/844

[56] References Cited

U.S. PATENT DOCUMENTS

| | | | |
|---|---|---|---|
| 2,170,185 | 8/1939 | Carpenter | 167/90 |
| 2,356,801 | 8/1944 | Travis et al. | 167/22 |
| 2,435,005 | 1/1948 | Huppke et al. | 167/90 |
| 2,853,423 | 9/1958 | La Via | 167/90 |
| 3,186,912 | 6/1965 | Beamer | 167/91 |
| 3,590,118 | 6/1971 | Conrady et al. | 424/19 |
| 3,821,363 | 6/1974 | Black et al. | 424/59 |
| 4,268,498 | 5/1981 | Gedeon et al. | 424/59 |
| 4,434,154 | 2/1984 | McShane | 424/60 |
| 4,477,467 | 10/1984 | Nishizawa et al. | 424/317 |
| 4,529,598 | 7/1985 | Wong | 514/277 |
| 4,701,321 | 10/1987 | Bernstein | 424/60 |
| 4,756,905 | 7/1988 | Melnik | 424/63 |
| 4,820,508 | 4/1989 | Wortzman | 424/59 |
| 5,518,712 | 5/1996 | Stewart | 424/59 |

*Primary Examiner*—Jose G. Dees
*Assistant Examiner*—Michael A. Williamson
*Attorney, Agent, or Firm*—Sanford J. Asman

[57] ABSTRACT

An improved sunscreen protection and insect repellent combination composition having an SPF factor of about 2 to about 50 and further having an unexpected, unusually long efficacy period when used in rainy conditions or prolonged periods of high humidity, such as in a tropical or sub-tropical rain forests, or the like, and after the wearer has been underwater. The composition forms a stable emulsion lotion that is easy to store. No special precautions are required by the person who applies the lotion. The composition includes a sunscreen agent, an insect repellent, an emulsifying agent, and a film former, all in an aqueous solvent. The composition forms a thin film on the skin, but it is non-greasy to the touch. The lotion is easily removed by scrubbing with soap and water.

20 Claims, No Drawings

WATER RESISTANT SUNSCREEN AND INSECT REPELLENT COMPOSITION

CROSS-REFERENCE TO RELATED APPLICATIONS

This is a Continuation-in-Part of application Ser. No. 08/154,584 filed Nov. 18, 1993, now U.S. Pat. No. 5,518,712, issued May 21, 1996, which was a Continuation-in-Part of U.S. patent application Ser. No. 07/904,514 filed Jun. 25, 1992, now abandoned.

FIELD OF THE INVENTION

This invention relates to a synergistic sunscreen and insect repellent composition, and in particular to an improved water resistant combination sunscreen and insect repellent composition. The compound is non-greasy, pleasant smelling, and sweet tasting with an approximate SPF factor of 15. Although the compound is highly water resistant, it is easily removed with soap and water and scrubbing.

BACKGROUND OF THE INVENTION

Insect borne diseases are a major non-battle injury threat to the military. Seven of the top eleven diseases that reduce military effectiveness are transmitted by insects. It is imperative for peak military operational efficiency that an acceptable insect repellent be produced to reduce the disease threat and to provide personal protection from insect borne diseases. The insect repellent must also meet the unique requirements necessary for personal protection of the armed forces. When considering the broad spectrum of use, the repellent should be long lasting and acceptable to the user. Also, the military spends long periods of time outdoors and accordingly, an acceptable sunscreen and insect repellent combination for use by field military personnel is highly desirable, particularly if it is compatible with other military materials, such as clothing and weapons. In other words, the composition should not have a negative effect on uniforms or the use and operation of weapons.

The military services have not developed a satisfactory sunscreen insect repellent composition that meets their unique operating needs.

A second major need exists for people who live and work and play in the outdoors. They have protected themselves from insects for years by using insect repellents. Likewise, people who live and play and work outdoors have used suntan compounds to accelerate the darkening of the exposed skin. Only recently the knowledge that the sun's ultraviolet rays causes skin cancer has caused people to switch from suntan lotions to sunscreening lotions that provide protection from the sun. These lotions are measured on a scale of increasing protection from 1 to 50. The scale is called the Sun Protection Factor ("SPF"). The SPF value of a sunscreen allows the consumer to determine the degree of sunburn protection that he or she is willing to accept for a given period of time in the direct exposure to the sun's ultraviolet rays.

Many civilian products have become commercially available in the recent past that combine sunscreen lotions and insect repellent lotions in one package. These products, for many reasons, are not completely satisfactory. Some of the reasons why they are not satisfactory are as set forth below.

First, the insect repellent compositions available are greasy, have a foul odor, and are usually effective only for short periods and require the person to continuously apply the lotion to maintain the desired degree of insect repellency on the skin. In many cases, as, for example, in a duck blind this is very inconvenient, because the person in the duck blind cannot repeatedly apply the insect repellent lotion while remaining perfectly motionless.

Second, many combination insect repellent and sunscreen compositions are easily removed with water. This is a particular problem in the summertime when the person sweats. The effectiveness of the insect repellent and sunscreen composition is dramatically reduced due to sweat removing the composition from the skin.

Third, most insect repellent compositions are oily and offensive to the olfactory system of the wearer as well as to those people who are around the wearer.

U.S. Pat. No. 2,170,185, entitled "MENTHYL ANTHRANILATE AND PROCESS OF PREPARING SAME", issued on Aug. 22, 1939 to M. S. Carpenter discloses a suntan cream having menthyl anthranilate which is a menthyl ester of anthranilic acid.

U.S. Pat. No. 4,434,154, entitled "TANNING AND ULTRA-VIOLET SCREENING COMPOSITION HAVING HIGH STABILITY", issued on Feb. 28, 1984 to J. E. McShane discloses a tanning and screening composition that is highly stable after prolonged storage. The composition is alleged to be useful, even after such prolonged storage, for shielding human skin from the harmful ultraviolet rays of the sun.

U.S. Pat. No. 4,701,321, entitled "LIQUID DETERGENT WITH SUNSCREEN AGENT", issued on Oct. 20, 1987 to J. E. Bernstein discloses a liquid detergent with a sunscreen agent selected from the aminobenzoic acid family, the other components of the composition being a preservative, a non-ionic detergent, an amphoteric detergent, or a mixture thereof in an aqueous vehicle.

U.S. Pat. No. 4,820,508, entitled "SKIN PROTECTIVE COMPOSITION", issued on Apr. 11, 1989 to M. S. Wortzman discloses a skin protective composition for topical application to protect human skin from infrared radiation. The composition contains titanium dioxide and mica or coated mica as its principal active reagents.

U.S. Pat. No. 4,756,905, entitled "INSECT-REPELLENT CAMOUFLAGE COMPOSITION", issued on Jul. 12, 1988 to J. Melnik discloses a composition for repelling insects and camouflaging the human skin. The insect repellent, N,N-diethyl-m-toluamide ("DEET"), and a camouflage pigment are combined along with an optional emulsifier to allow a single application to serve both the camouflage and insect repellent functions.

U.S. Pat. No. 3,590,118, entitled "LONG LASTING INSECT REPELLENT FILMS FOR SKIN AND OTHER SUBSTRATES", issued on Jun. 29, 1971 to J. A. Conrady, et al. discloses a long lasting insect repellent film for skin application. The active chemical agents are dissolved in interpolymer resins to provide a slow release system for the active chemical agents when spread and dried as a film on a human being. The coating can be applied by spraying or spreading and it is alleged to be easily removable with a soapy water solution.

U.S. Pat. No. 3,821,363, entitled "SUNSCREEN PREPARATION EMPLOYING ETHYLENE-MALEIC ANHYDRIDE COPOLYMERS", issued on Jan. 27, 1974 to A. S. Black, et al. discloses a gel of the acid of a cross-linked copolymer of ethylene-maleic anhydride that includes a sunscreen agent. The gel is alleged to be substantially free of any emulsifying agent.

U.S. Pat. No. 2,435,005, entitled "SKIN PROTECTIVE OINTMENT", issued on Jan. 27, 1948 to W. F. Huppke, et al. discloses a cream or ointment containing a film-former so that the cream or ointment forms a film on the wearer's skin. The cream or ointment may include an insect repellent or a sunscreen, or both. Preferably, the film former is a mixture of ethyl cellulose and shellac.

U.S. Pat. No. 2,853,423, entitled "AEROSOL SUNSCREENING COMPOSITION", issued on Sep. 23, 1958 to A. L. La Via discloses an aerosol composition alleged to be useful in protecting against sunburn.

U.S. Pat. No. 4,477,467, entitled "INSECT REPELLENT", issued on Oct. 16, 1984 to K. Nishizawa, et al. discloses the use of DEET in combination with certain proton acceptors for the purpose of inhibiting the absorption of DEET into the wearer's skin.

U.S. Pat. No. 2,356,801, entitled "INSECT REPELLENT COMPOSITION", issued on Aug. 29, 1994 to B. V. Travis, et al. discloses an insect repellent composition in which four insect repellent compounds are combined to improve the effectiveness of the composition.

None of these previous efforts, however, provides the benefits provided by the present invention. Additionally, the prior art does not teach or suggest the present inventive combination of component elements, as disclosed and claimed herein. The present invention achieves its intended purposes, objectives and advantages over the prior art compositions through a new, useful and unobvious combination of component elements. The present invention is simple to use, it contains a minimum number of functioning ingredients, it has reasonable manufacturing, testing and packaging costs, and it uses only readily available materials.

In particular, the prior art does not teach a combination sunscreen and insect repellent composition that is a stable emulsion which, when on a wearer's skin, promotes waterproofing and maintains its SPF for protracted periods of time.

Although there have been many inventions related to sunscreen protection and insect repellent compositions, none of the prior art has provided an effective, low cost and reliable product which has achieved general use.

SUMMARY OF THE INVENTION

The present invention meets the requirements of long lasting efficacy under extreme environmental conditions, low initial cost, and water resistance. Further, the composition is non-greasy, sweet tasting, easy to apply, and pleasing to the olfactory senses.

In brief, the invention is a sunscreen and insect repellent composition having an extremely long efficacy period when used in rainy conditions and prolonged periods of high humidity, as in tropical and sub-tropical rain forests, even after the wearer has been under water. The composition includes a sunscreen agent present in an amount effective to provide an SPF of between about 2 and about 50, and preferably in the range of between about 15 and about 30. An insect repellent agent constitutes between about 7% to about 33% by weight of the composition. The composition further includes a plurality of ingredients contributing to the composition's synergistically long efficacy period. In particular, these ingredients are an emulsifying agent (for forming a stable emulsion) and a film forming agent (so that the composition forms a film when applied to a wearer's skin).

The composition forms a stable emulsion lotion that is easy to store. Proper application of the lotion requires little or no training or special precautions. When applied, a thin film is formed on the skin that is non-greasy to the touch and resists water, yet it is readily removed by scrubbing with soap and water.

The resultant composition has an extremely long efficacy period even when subjected to extreme environmental conditions of high humidity, and even when the wearer goes under water. Further, the composition was tested exhaustively under strict laboratory and field conditions using the appropriate protocols that are approved by the U.S. Army Medical Material Development Activity and performed superior to any other product tested to date.

The foregoing has outlined rather broadly the more pertinent and important features of the present invention in order that the detailed description of the invention that follows may be better understood so that the present contribution to the art can be more fully appreciated. Additional features of the invention, described hereinafter, form the subject of the claims of the invention. It should be appreciated by those skilled in the art that the conception and the specific embodiments disclosed may be readily utilized as a basis for modifying or designing other compositions for carrying out the same purposes as the present invention. It should also be realized by those skilled in the art that such equivalent compositions do not depart from the spirit and scope of the invention as set forth in the appended claims.

DETAILED DESCRIPTION OF THE PREFERRED EMBODIMENT

The present invention is a stable emulsion composition that provides protection from the sun's ultraviolet rays while simultaneously acting as an insect repellent. The composition includes a sunscreen agent, an insect repellent agent, an emulsifying agent, and a film forming agent, all in an aqueous solvent. The composition can also include a thickener, at least one fragrance, and at least one sweetener.

In a preferred embodiment of the invention, the insect repellent agent is N,N-diethyl-m-toluamide ("DEET") present in an amount ranging from about 7% to about 33% by weight (wt %). Other insect repellents, such as citronella, can be used. However, DEET is currently the most effective insect repellent compound which is known, and presently approved for such use. The amount of DEET in the composition preferably ranges from about 12 wt % to about 22 wt %. In the most preferred embodiment, DEET comprises about 17 wt %.

The sunscreen agent should provide an SPF of from about 2 to about 50. A preferred embodiment of the invention provides an SPF of from about 15 to about 30. It is also preferred that a sunscreen agent be used that provides protection from radiation from about 290 nm to 340 nm. In order to achieve this SPF in the presence of 12 wt % to 22 wt % DEET, in a preferred embodiment three sunscreens are used that have different absorption peaks. Octyl methoxycinnamate (ethylhexyl p-methoxycinnamate), a shorter untraviolet ("UV") wavelength, or UV-B absorber, is used in an amount from about 2 wt % to about 8 wt %. Octyl salicylate, a UV-B absorber, is used in an amount from about 3 wt % to about 5 wt %. Oxybenzone (benzophenone-3), a longer UV wavelength, or UV-A absorber, is used in an amount from about 2 wt % to about 6 wt %. Other sunscreens can be used in the invention. The type and the amount of sunscreen agent can vary depending upon the degree of protection desired. For example, the sunscreen agent may comprise a member of the group consisting of menthyl anthranilate, dioxybenzone, aminobenzoic acid, amyl dimethyl PABA, diethanolamine p-methoxy cinnamate, ethyl 4-bis(hydroxypropyl) aminobenzoate, 2-ethylhexy 1-2-cyano-3,3-diphenylacrylate, homomenthyl salicylate, glyceryl aminobenzoate, dihydroxyacetone, octyl dimethyl PABA, 2-phenylbenzimidazole-5-sulfonic acid, triethanolamine salicylate, zinc oxide, and titanium oxide.

In a preferred embodiment of the invention, a combination of emulsifiers is used to achieve the desired result of a stable emulsion containing from about 7 wt % to about 33 wt % insect repellent and a sunscreen agent in an amount sufficient to provide an SPF from about 2 to about 50. An ethoxylated fatty acid ester such as polyethylene glycol stearate (40:1) (PEG 40 stearate), is used in an amount of from about 0.10 wt % to about 0.20 wt % or, preferably, about 0.15 wt %. This compound is a non-ionic oil and water emulsifier. An example of such a compound is MYRJ® 52S, distributed by ICI Americas, Inc. in Wilmington, Del. Primarily, MYRJ® 52S is known for its emulsification qualities and, typically, MYRJ® 52S is used for general skin formulations including facial lotions and skin moisturizers and the like. Any similar compound can be used in the present invention.

A hydrophobically modified acrylic acid co-polymer is added as an emulsifier in an amount of about 5 wt % to about 25 wt % or, preferably, about 15 wt %, of a 2% solution. An example of such a compound is PEMULEN TR1®, distributed by the B. F. Goodrich Company in Akron, Ohio. This compound is more specifically an acrylic acid-stearyl methacrylate copolymer and it is known mainly for its emulsifying and stabilizing properties. Typically, PEMULEN TR1® is used in perfumes, in hair glossing compositions, and in elegant skin care moisturizing compositions.

Other emulsifying agents can be used, such as, for example, AMPHISOL™-diethanolamine cetyl phosphate—an anionic emulsifier; SEPIGEL™—manufactured by Seppic Company, an acrylic acid polymer; KELTROL® T (2% solution), a natural gum thickener and emulsifier, distributed by Monsanto Company of St. Louis, Mo.; PROMULGEN® D, a non-ionic emulsifier distributed by Union Carbide Chemicals and Plastics Technology Corporation; and ARLACEL® 165, a non-ionic emulsifier distributed by ICI Americas, Inc. of Wilmington, Del.

A CARBOPOL® is preferably added to the composition in an amount of about 2 wt % to about 10 wt %, or preferably, about 5 wt %, of a 2% solution to provide suspending, thickening, and stabilizing properties. CARBOPOL® is a trademark of B. F. Goodrich Company for a group of water soluble carboxy vinyl polymers. Another thickening agent that can be used is KELTROL® T (2% solution) a natural gum polysaccharide.

A film former is added to the composition so that the composition forms a film when applied to the skin. The film former also adds waterproofing properties to the composition. An example of an appropriate film former is poly(vinyl pyrrolidone/1-triacontene) (Tricontonyl PVP), added at about 3 wt %. This compound contributes film forming and water-proofing qualities to the composition. An example of such a compound is GANEX® WP 660, a film-forming waterproofing agent distributed by GAF Chemicals Corporation. Primarily, it is used for high quality waterproofing sunscreen formulations. Other film formers known in the art can be used advantageously in the composition. These include acrylate copolymers, acrylate/octylacrylamide copolymers, acrylate/VA copolymer, amodimethicone, AMP/acrylate copolymers, behenyl beeswax, behenyl/isostearyl, beeswax, butylated PVP, butyl ester of PVM/MA copolymers, calcium/sodium PVM/MA copolymers, dimethicone, dimethicone copolyol, dimethicone/mercaptopropyl methicone copolymer, dimethicone propylethylenediamine behenate, dimethicolnol ethylcellulose, ethylene/acrylic acid copolymer, ethylene/MA, copolymer, ethylene/VA copolymer, fluoro C2-8 alkyldimethicone, hexanediol beeswax, hydrogenated styrene/butadiene copolymer, hydroxyethyl ethylcellulose, isobutylene/MA copolymer, laurylmethicone copolyol, methyl methacrylate crosspolymer, methylacryloyl ethyl betaine/acrylates copolymer, microcrystalline wax, nitrocellulose, octadecene/MA copolymer, octadecene/maleic anhydride copolymer, octylacrylamide/acrylate/butylaminoethyl methacrylate copolymer, oxidized polyethylene, perfluoropolymethylisopropyl ether, polyacrylic acid, polyethylene, polymethyl methacrylate, polypropylene, polyquaternium-10, polyquaternium-11, polyquaternium-28, polyquaternium-4, PVM/MA decadiene crosspolymer, PVM/MA copolymer, PVP, PVP/decene copolymer, PVP/dicosene copolymer, PVP/hexadecene copolymer, PVP/MA copolymer, PVP/VA copolymer, silica, silica dimethyl silylate, sodium acrylate/vinyl alcohol copolymer, stearoxy dimethicone, stearoxytrimethylsilane, stearyl alcohol, stearylvinyl ether/MA copolymer, styrene/DVB copolymer, styrene/MA copolymer, tetramethyl tetraphenyl trisiloxane, tricontanyl trimethyl pentaphenyl trisiloxane, trimethylsiloxysilicate, VA/crotonates copolymer, VA/crotonates/vinyl proprionate copolymer, VA/butyl maleate/isobornyl acrylate copolymer, vinyl caprolactam/PVP/dimethylaminoethyl methacrylate copolymer, and vinyldimethicone.

The above ingredients are combined in an aqueous solvent, such as a mixture of water and propylene glycol. Other stabilizing ingredients, such as tetrasodium EDTA and cetearyl alcohol, are preferably added. Triethanolamine can be added as a stabilizer and to adjust the pH. Further, an emollient such as seamollient, vitamin E acetate, cyclomethicone silicon (DC 344), or the like can be added. A fragrance, a sweetener, and a preservative, such as GERMABEN® II, can also be added to the composition. GERMABEN® II is a bactericide and fungicide distributed by GAF Chemicals Corporation.

The resulting composition produced in accordance with the present invention has the desired characteristics of providing a non-greasy, insect repellent and sunscreen composition with an appropriate SPF. The composition forms a lotion that is easy to store. Proper application of the lotion requires little or no training. No special precautions are required by the person who applies the lotion. Further, the resultant composition has the synergistic attribute of having an extremely long efficacy period when used in rainy conditions or prolonged periods of high humidity, such as the conditions found in tropical and sub-tropical rain forests or the like, or when the lotion is worn under water. The compound forms a thin, water resistant film on the skin. Yet it is readily removed by scrubbing with soap and water.

Compositions according to the following formulae were prepared.

EXAMPLE I

|  | WEIGHT % |
|---|---|
| PHASE A | |
| Deionized Water | 32.53 |
| Propylene Glycol | 2.50 |
| CARBOPOL ® 940 (2% Solution) | 5.00 |
| PEMULEN TR1 ® (2% Solution) | 15.00 |

-continued

| | WEIGHT % |
|---|---|
| Seamollient | 1.00 |
| Tetrasodium EDTA | 0.10 |
| PHASE B | |
| N,N-diethyl-m-toluamide (DEET) | 17.00 |
| Cetearyl Alcohol | 3.50 |
| Octyl Methoxycinnamate (Neoheliopan AV) | 7.50 |
| Octyl Salicyate (Neoheliopan OS) | 5.00 |
| PEG 40 Stearate (MYRJ ® 52S) | 0.15 |
| Oxybenzone | 6.00 |
| Poly/vinyl pyrrolidone/1-triacontene) | |
| GANEX ® WP-660 | 3.00 |
| Vitamin E Acetate | 0.25 |
| PHASE C | |
| Triethanolamine 99% | 0.11 |
| PHASE D | |
| Citronella Java | 0.01 |
| Fragrance MF 3871 | 0.25 |
| PHASE E | |
| Sodium Saccharin | 0.10 |
| PHASE F | |
| GERMABEN ® II | 1.00 |

The mixing is done in a conventional manner and the ingredients in each phase are mixed in the sequence described below. The choice of the particular material used dictates the mixing time and temperature change rates.

A water phase was prepared by mixing the water and propylene glycol and heating to 75° C. with propeller agitation in a stainless steel kettle large enough to hold the entire batch. CARBOPOL® 940 and PEMULEN TR1® were slowly sifted into the mixture. Then, seamollient and disodium EDTA were added uniformly to form a first interim mixture. The first interim mixture was mixed while maintaining the temperature in the kettle at 75° C. for 30 minutes.

Next an oil phase was prepared by combining DEET, cetearyl alcohol, octyl methoxycinnamate, octyl salicylate, MYRJ® 52S, oxybenzone, GANEX® WP-660, and vitamin E acetate in a second initial mixture with slow agitation in a second stainless steel kettle and heated to 85° C. The ingredients in the second kettle were mixed for 30 minutes at 85° C. After 30 minutes, the second initial mixture in the second kettle was added to the interim mixture in the first kettle and a second interim mixture was formed. The second interim mixture was mixed for 30 minutes. Then, triethanolamine was added to the second interim mixture in the first kettle using a slow sidesweep agitation to produce a third interim mixture. The third interim mixture in the kettle was mixed for 30 minutes while maintaining the temperature at 75° C. Then, the third interim mixture in the kettle was cooled to 45° C. while stirring slowly. Citronella, fragrance, saccharin and GERMABEN® II were then slowly added to the third interim mixture in the kettle to produce a resultant mixture.

The resultant mixture in the first kettle was mixed for 20 minutes to provide uniformity and then the resultant mixture was passed through a Gifford-Wood colloid mill with a narrow setting for providing a small particle size. The resultant mixture was recirculated in the first kettle until homogeneity was achieved.

EXAMPLE 2

| | WEIGHT % |
|---|---|
| PHASE A | |
| Deionized Water | 37.79 |
| Propylene Glycol | 1.00 |
| CARBOPOL ® 940 (2% Solution) | 7.50 |
| PEMULEN TR1 ® (2% Solution) | 7.50 |
| Seamollient | 0.10 |
| PHASE B | |
| DEET | 20.00 |
| Cetearyl Alcohol | 2.00 |
| Octyl Methoxycinnamate (Neoheliopan AV) | 7.50 |
| Octyl Salicyate (Neoheliopan OS) | 5.00 |
| Oxybenzone | 6.00 |
| GANEX ® WP-660 | 3.00 |
| Vitamin E Acetate | 0.10 |
| AMPHISOL ™ | 1.75 |
| Citronella | 0.01 |
| PHASE C | |
| Fragrance MF-3871 | 0.25 |
| PHASE D | |
| GERMABEN ® II | 1.00 |

The composition was prepared similar to Example 1. The ingredients of Phase A were combined and heated to 85° C. Phase B ingredients were heated to 90° C. and held at that temperature for 20 minutes. Phase B was added to Phase A, the combined mixture was cooled to 45° C. with high speed agitation, at which point the ingredients of Phases C and D were added. The pH of the final composition was 4.94.

EXAMPLE 3

| | WEIGHT % |
|---|---|
| PHASE A | |
| Deionized Water | 44.79 |
| Propylene Glycol | 1.00 |
| Seamollient | 0.10 |
| PHASE B | |
| DEET | 10.00 |
| Cetearyl Alcohol | 2.00 |
| Menthyl Antranilate | 5.00 |
| Octyl Methoxycinnamate (Neoheliopan AV) | 7.50 |
| Oxybenzone | 3.00 |
| GANEX ® V-220 | 1.50 |
| Vitamin E Acetate | 0.10 |
| AMPHISOL ™ | 1.75 |
| PHASE C | |
| SEPIGEL 305 ™ | 2.00 |
| PHASE D | |
| Citronella | 0.01 |
| PHASE E | |
| Fragrance MF-3871 | 0.25 |
| PHASE F | |
| GERMABEN ® II | 1.00 |
| PHASE G | |
| DEET Powder (CLI 7201/1) | 20.00 |

Phase A ingredients were combined and heated to 85° C. Phase B ingredients were combined and heated to 90° C. and held at that temperature, with stirring, for 20 minutes. Phase B was added to Phase A with high speed agitation. Phase C was added with high speed agitation. The mix was cooled to 45° C. while stirring and phases D, E. and F were added with high speed agitation. Phase G was mixed in to homogeneity. The final pH was 6.2.

EXAMPLE 4

| | WEIGHT % |
|---|---|
| PHASE A | |
| Deionized Water | 34.90 |
| KELTROL ® T (2% solution) | 15.00 |
| Propylene Glycol | 1.00 |
| PHASE B | |
| DEET | 30.00 |
| Cetearyl Alcohol | 1.00 |
| Octyl Methoxycinnamate (ESCALOL 507) | 8.00 |
| Oxybenzone | 4.00 |
| Vitamin E Acetate | 0.10 |
| AMPHISOL ™ | 1.50 |
| ARLACEL ® 165 | 0.50 |
| PHASE C | |
| SEPIGEL 305 | 3.00 |
| PHASE D | |
| GERMABEN ® II | 1.00 |

Phase A ingredients were combined and heated to 85° C. Phase B ingredients were combined and heated to 90° C. and held for 20 minutes with stirring. Phase B was added to Phase A with high speed agitation. Phase C was added with high speed agitation and the mix was cooled to 45° C. while high speed agitation was maintained. Phase D was added and the mix homogenized. The final pH was 6.04.

EXAMPLE 5

| | WEIGHT % |
|---|---|
| PHASE A | |
| Deionized Water | 44.90 |
| KELTROL ® T (2% solution) | 15.00 |
| Propylene Glycol | 1.00 |
| PHASE B | |
| DEET | 20.00 |
| Cetearyl Alcohol | 1.00 |
| Octyl Methoxycinnamate (ESCALOL 507 ™) | 8.00 |
| Oxybenzone | 4.00 |
| Vitamin E Acetate | 0.10 |
| AMPHISOL ™ | 1.50 |
| ARLACEL ® 165 | 0.50 |
| PHASE C | |
| SEPIGEL 305 ™ | 3.00 |
| PHASE D | |
| GERMABEN ® II | 1.00 |

Phase A ingredients were combined and heated to 85° C. Phase B ingredients were combined and heated to 90° C. and held for 20 minutes with stilling. Phase B was added to Phase A with high speed agitation. Phase C was added with high speed agitation and the mix was cooled to 45° C. while high speed agitation was maintained. Phase D was added and the mix homogenized. The final pH was 6.24.

RESULTS

The compositions were evaluated under appropriate protocols for measuring the efficacy of sunscreen formulations and insect repellent formulations against mosquitoes. Cage tests were conducted at Walter Reed Army Hospital. Ten mosquitoes in each of seven cages were exposed to both a treated (0.1 ml composition) forearm and an untreated forearm of a human volunteer. The test was conducted for five minutes per cage unless three bites were received by the volunteer before the five minutes were up. The treated forearms received no bites in any of the tests while the untreated forearms received three bites in each of the tests. Then, the compositions were tested under strict field conditions using appropriate protocols that are approved by the U.S. Army Medical Material Development Activity. The field tests were conducted at the U.S. Army testing facilities in Alaska, Thailand, and South America Immersion tests were conducted to determine the waterproofing effectiveness of the compositions. Five test subjects were immersed in a whirlpool for a total of eighty (80) minutes. The initial SPF factor prior to immersion was 16.1. The measurements were taken at 20 minute intervals on all 5 test subjects. The interim SPF factor and final SPF factor was 16.1 in all cases.

When a person applies the compositions outlined in the Examples to the exposed parts of the body, according to the method disclosed herewith, a thin film forms on the skin that provides a non-greasy, pleasant smelling insect repellent and a sweet tasting sunscreen protectant. The compositions have the unexpected property of having an extremely long efficacy period, even when subjected to extreme temperature and humidity, and even when the exposed body parts have been under water for extended periods of time. The synergistic result of combining the hydrophobically modified acrylic acid copolymer, ethoxylated fatty acid ester and film former in the quantities disclosed in the Examples, and preparing the compositions according to the steps disclosed herein provide the invention with unexpected superior insect repellent and sunscreen properties, which are superior to any which were previously known.

The combination of the ethoxylated fatty acid ester, hydrophobically modified acrylic acid copolymer, film former, oxybenzone and DEET would not normally be expected to form an emulsion when combined. However, by combining them in the ratios disclosed, a stable emulsion is formed. This emulsion when rubbed onto the skin "breaks down" as the hydrophobically modified acrylic acid copolymer is precipitated by the salt on the skin which breaks down the emulsion leaving an insufficient amount of emulsifier on the skin to wash off when the wearer sweats or enters the water. Additionally, the film former combines with the DEET and the sunscreen to form a uniformly thick, waterproof sunscreen film. The increased thickness of the film allows for enhanced SPF performance since the optical path length of the UV radiation is increased and thus, the sunscreen absorbs the UV more efficiently.

The prior art does not reveal or even suggest a motivation for combining the above-cited ingredients. The inventor experimented with various compositions in order to develop the invention. It was only after numerous failed attempts that the invention was finally achieved.

The present disclosure includes that contained in the appended claims, as well as that of the foregoing description. Although this invention has been described in its preferred form with a certain degree of particularity, it is understood that the present disclosure of the preferred form has been made only by way of example, and that numerous changes in the details of compositions and the combination of individual ingredients may be resorted to without departing from the spirit or scope of the invention.

I claim:

1. A waterproof sunscreen and insect repellent stable emulsion composition, comprising:

(a) a sunscreen agent present in an amount effective to provide an SPF of from 5 to about 50;

(b) an insect repellent agent present in an amount from about 7 wt % to about 33 wt %;

(c) a water based solvent;

(d) an emulsifying agent for forming a stable emulsion; and (e) a film forming agent present in an amount effective to form a thin film when the composition is applied to the skin of a person.

2. The composition of claim 1, wherein said sunscreen agent is present in an amount effective to provide an SPF of from about 15 to about 30.

3. A sunscreen and insect repellent composition prepared by a method comprising the steps of:

(a) preparing a water phase comprising an aqueous solvent and a hydrophobically modified acrylic acid copolymer;

(b) preparing an oil phase comprising an insect repellent agent, a sunscreen agent, an ethoxylated fatty acid ester, and a film former; and (c) combining said oil phase with said water phase to form a stable emulsion.

4. A waterproof sunscreen and insect repellent composition for applying to the skin of a person, comprising:

(a) a sunscreen agent present in an amount effective to provide an SPF of from about 15 to about 30;

(b) DEET present in an amount of from about 12 wt % to about 22 wt %;

(c) a water based solvent;

(d) an emulsifying agent in an amount effective to form a stable emulsion; and (e) a film forming agent in an amount effective to form a thin film on the skin of a person, wherein the composition is waterproof and will remain on the skin and provide said SPF even after the skin of the person on whom the composition has been applied has been submerged under water for at least about one hour.

5. The composition of claim 4, wherein said sunscreen agent comprises octyl methoxycinnamate, octyl salicylate, and oxybenzone.

6. The composition of claim 4, wherein said film forming agent comprises poly(vinyl pyrrolidone/1-triacontene) present in an amount from about 1 wt % to about 5 wt %.

7. The composition of claim 4, further comprising at least one thickening agent.

8. The composition of claim 7, further comprising at least one fragrance, at least one emollient, at least one sweetener, and at least one preservative.

9. A waterproof sunscreen and insect repellent stable emulsion composition, comprising:

(a) a sunscreen agent comprising from about 2 wt % to about 8 wt % octyl methoxycinnamate, from about 3 wt % to about 5 wt % octyl salicylate, and from about 2 wt % to about 6 wt % oxybenzone;

(b) an insect repellent agent present in an amount from about 7 wt % to about 33 wt %;

(c) a water based solvent;

(d) an emulsifying agent for forming a stable emulsion; and (e) a film forming agent present in an amount effective to form a thin film when the composition is applied to the skin of a person.

10. A waterproof sunscreen and insect repellent stable emulsion composition, comprising:

(a) a sunscreen agent present in an amount effective to provide an SPF of from 5 to about 50;

(b) an insect repellent agent comprising DEET;

(c) a water based solvent;

(d) an emulsifying agent for forming a stable emulsion; and (e) a film forming agent present in an amount effective to form a thin film when the composition is applied to the skin of a person.

11. The composition of claim 10 wherein said DEET is present in an amount from about 7 wt % to about 33 wt %.

12. The composition of claim 10, wherein said DEET is present in an amount from about 12 wt % to about 22 wt %.

13. The composition of claim 10, wherein said insect repellent agent further comprises citronella.

14. A waterproof screen and insect repellent stable emulsion composition, comprising:

(a) a sunscreen agent present in an amount effective to provide an SPF of from 5 to about 50;

(b) an insect repellent agent present in an amount from about 7 wt % to about 33 wt %;

(c) a water based solvent;

(d) an emulsifying agent comprising an ethoxylated fatty acid ester and a hydrophobically modified acrylic acid copolymer for forming a stable emission; and (e) a film forming agent present in an amount effective to form a thin film when the composition is applied to the skin of a person.

15. The composition of claim 14, wherein said ethoxylated fatty acid ester comprises a polyethylene glycol stearate.

16. The composition of claim 14, wherein said hydrophobically modified acrylic acid copolymer comprises an acrylic acid-stearyl methacrylate copolymer.

17. A waterproof sunscreen and insect repellent stable emulsion composition, comprising:

(a) a sunscreen agent present in an amount effective to provide an SPF of from 5 to about 50;

(b) an insect repellent agent present in an amount from about 7 wt % to about 33 wt %;

(c) a water based solvent;

(d) an emulsifying agent for forming a stable emulsion; and (e) a film forming agent comprising poly(vinyl pyrrolidone/1-triacontene) to form a thin film when the composition is applied to the skin of a person.

18. The waterproof sunscreen and insect repellent stable emulsion composition of claim 17 wherein said poly(vinyl pyrrolidone/1-triacontene) is present in an amount from about 1 wt % to about 5 wt %.

19. A waterproof sunscreen and insect repellent stable emulsion composition, comprising:

(a) a sunscreen agent present in an amount effective to provide an SPF of from 5 to about 50;

(b) an insect repellent agent present in an amount from about 7 wt % to about 33 wt %;

(c) a water based solvent;

(d) an emulsifying agent for forming a stable emulsion;

(e) a film forming agent present in an amount effective to form a thin film when the composition is applied to the skin of a person; and (f) a thickening agent.

20. The composition of claim 19, wherein said thickening agent comprises a carboxy vinyl polymer present in an amount of about 0.3 wt %.

* * * * *